(12) United States Patent
Henschel

(10) Patent No.: US 12,702,848 B2
(45) Date of Patent: Aug. 11, 2026

(54) STACKABLE CAPACITOR FOR AN IMPLANTABLE MEDICAL DEVICE

(71) Applicant: BIOTRONIK SE & CO. KG, Berlin (DE)

(72) Inventor: Martin Henschel, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 723 days.

(21) Appl. No.: 16/573,221

(22) Filed: Sep. 17, 2019

(65) Prior Publication Data

US 2020/0086131 A1 Mar. 19, 2020

(30) Foreign Application Priority Data

Sep. 18, 2018 (EP) .................................... 18195211

(51) Int. Cl.
*A61N 1/39* (2006.01)
*H01G 9/008* (2006.01)
*H01G 9/08* (2006.01)
*H01G 9/14* (2006.01)
*H01G 9/28* (2006.01)

(52) U.S. Cl.
CPC ......... *A61N 1/3968* (2013.01); *A61N 1/3956* (2013.01); *H01G 9/008* (2013.01); *H01G 9/08* (2013.01); *H01G 9/14* (2013.01); *H01G 9/28* (2013.01)

(58) Field of Classification Search
CPC ................................ H01G 9/08; H01G 9/008
See application file for complete search history.

(56) References Cited

U.S. PATENT DOCUMENTS 5,522,851 A * 6/1996 Fayram ................ A61N 1/3956 607/2
5,814,082 A 9/1998 Fayram et al.
6,979,356 B1 * 12/2005 Carson ..................... H01G 9/12 29/25.03
7,031,139 B1 4/2006 Fayram
9,859,065 B1 * 1/2018 Lim ......................... H01G 9/08
2003/0058606 A1 * 3/2003 O'Phelan ................. H01G 9/08 361/509
2003/0204216 A1 * 10/2003 Ries ................... A61N 1/37512 607/36
2005/0154423 A1 * 7/2005 Goedeke ............. A61N 1/3758 607/36

(Continued)

*Primary Examiner* — David M Sinclair
(74) *Attorney, Agent, or Firm* — Laurence A. Greenberg; Werner H. Stemer; Ralph E. Locher

(57) ABSTRACT

A capacitor for an implantable medical device has a housing. The housing has a first outer side and a second outer side facing away from the first outer side. The two outer sides are connected to one another via a lateral outer side of the housing running in a circumferential direction of the housing. The lateral outer side has a straight first portion and an arcuate second portion. The first portion has two end regions, which are connected to one another via a middle region of the first portion. The end regions are each connected to the second portion. The capacitor has an electrical terminal arranged on the middle region of the first portion of the lateral outer side, which electrical terminal has two contact surfaces for electrically contacting the capacitor. A capacitor assembly and an implantable medical device are formed with the above describe capacitor.

6 Claims, 4 Drawing Sheets

(56) References Cited

U.S. PATENT DOCUMENTS

| | | | | |
|---|---|---|---|---|
| 2006/0061938 | A1 | 3/2006 | Dombro et al. | |
| 2008/0170353 | A1* | 7/2008 | Swanson | H01G 9/08<br>361/522 |
| 2017/0076874 | A1 | 3/2017 | O'Phelan et al. | |
| 2017/0207031 | A1* | 7/2017 | Eidelman | H01G 9/035 |
| 2018/0033561 | A1* | 2/2018 | McCurry | H01G 9/08 |

* cited by examiner

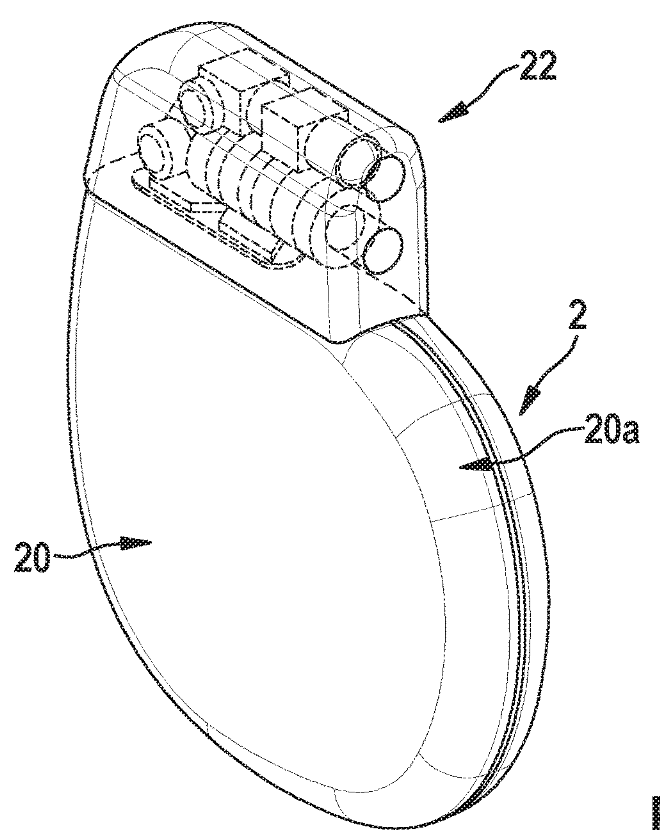
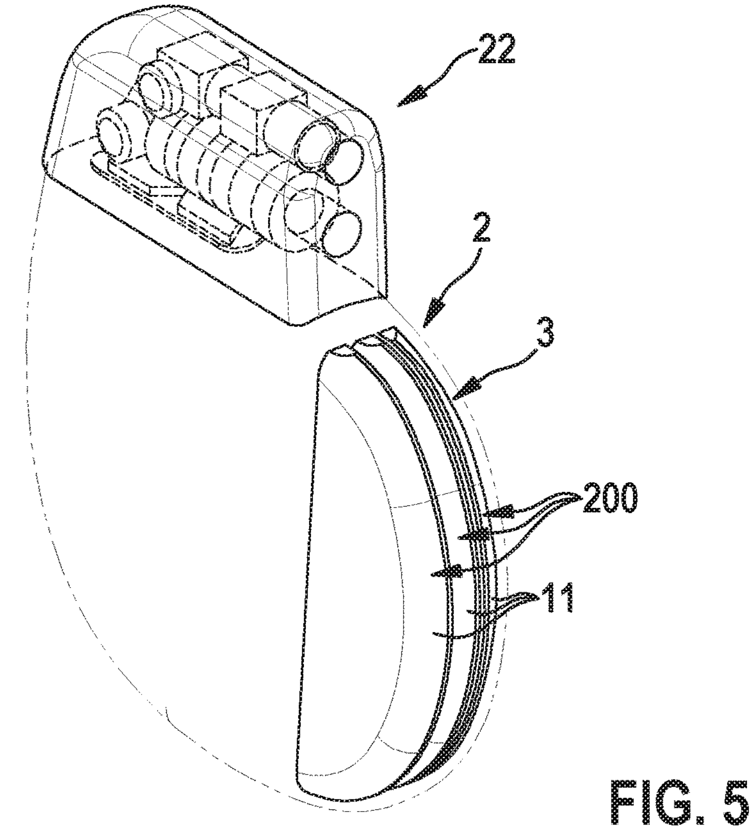
FIG. 5

STACKABLE CAPACITOR FOR AN IMPLANTABLE MEDICAL DEVICE

CROSS-REFERENCE TO RELATED APPLICATION

This application claims the priority, under 35 U.S.C. § 119, of European application EP 18195211.0, filed Sep. 18, 2018; the prior application is herewith incorporated by reference in its entirety.

BACKGROUND OF THE INVENTION

Field of the Invention

The present invention relates to a capacitor, a capacitor assembly, and an implantable medical device which comprises a capacitor assembly according to the invention or a capacitor according to the invention.

With regard to the arrangement of capacitors in a device housing of a medical device of this kind, it is known from the prior art to stack three structurally similar cuboid capacitors on top of one another in the same orientation. Alternatively, two structurally similar capacitors and a mirrored structure are also arranged in a triple stack in order to attain rounded outer radii at the upper side and the lower side of the stack.

If three structurally similar capacitors are stacked one above the other in the same orientation, it is not possible to attain an ergonomic rounding at the lower side if the upper side of each capacitor is rounded. In the case of a non-symmetrical capacitor contour, a mirrored capacitor would have to be developed for the lower side, which would disadvantageously increase the development effort and the component diversity. In order to reduce the development effort and the component diversity, three structurally similar capacitors were therefore used hitherto, at the expense of a less ergonomic housing design.

U.S. patent publication No. 2017/0076874 A1 also describes a stack of semi-circular foils which form a capacitor which has an electrical terminal in a corner region of a housing of the capacitor.

SUMMARY OF THE INVENTION

On this basis, the objective of the present invention is to provide a capacitor, a capacitor assembly, and an implantable medical device comprising such a capacitor assembly, wherein the capacitor is designed such that it can be stacked in a space-saving manner and at the same time can be well integrated into a device housing of an implantable medical device.

This objective is achieved by a capacitor having the features of the independent capacitor claim, a capacitor assembly having the features of the independent capacitor assembly claim, and by a medical device having the features of the independent medical device claim.

Advantageous embodiments of these aspects of the invention are detailed in the corresponding dependent claims and will be described hereinafter.

Accordingly, a capacitor is disclosed, comprising a housing where the housing has a first outer side and a second outer side facing away from the first outer side. The two outer sides are connected to one another via a lateral outer side of the housing running in a circumferential direction of the housing, and the lateral outer side has a planar first portion and an arcuate second portion. The first portion has two end regions, which are connected to one another via a middle region of the first portion. The end regions are each connected to the second portion. The capacitor has an electrical terminal arranged on the middle region of the first portion of the lateral outer side, which electrical terminal has two contact surfaces for electrically contacting the capacitor, wherein particularly the two contact surfaces are designed as planar surfaces.

A capacitor of this kind can be arranged advantageously in a triple stack, such that both the upper side of the capacitor stack and the lower side of the stack can have roundings. The surrounding device housing of an implantable medical device can then follow this capacitor contour likewise with large outer radii. If the capacitor is arranged within an implantable device, by way of the large outer radii of the rounding an outer housing for the implantable device can be designed such that advantages are created for the implant wearer, since the wearing comfort under the skin is increased compared to an implant housing having smaller outer radii and a smaller rounding.

In accordance with an embodiment of the capacitor according to the invention, it is provided that the capacitor is stackable, wherein the first or the second outer side of the capacitor forms a contact surface for a first or a second outer side of a structurally similar further capacitor. Particularly, the stackable capacitor can have the form of a flat semi-circular cylinder.

It is furthermore provided in accordance with an embodiment of the capacitor according to the invention that the housing of the capacitor is symmetrically identical with respect to a plane of symmetry running perpendicularly to the first portion of the lateral outer side and perpendicularly to the first and the second outer side.

It is furthermore provided in accordance with an embodiment of the capacitor according to the invention that the first and/or the second outer side are/is semi-circular.

It is furthermore provided in accordance with an embodiment of the capacitor according to the invention that the second portion of the lateral outer side forms, with the first outer side, a rounded housing edge of the housing of the capacitor. Here, the radius of the rounding of this edge is preferably above 2 mm.

In accordance with an embodiment, the rounding radius lies proportionately in the range of 16% to 33% of the thickness of a corresponding implantable device. The ratio is selected such that, with increased wearing comfort for the implant wearer, the space inside an implant is filled by the capacitor.

It is furthermore provided in accordance with an embodiment of the capacitor according to the invention that the first portion of the lateral outer side has a center point in the circumferential direction, and that the electrical terminal has a center point in the circumferential direction. The center point of the electrical terminal in the circumferential direction is arranged offset relative to the center point of the first portion, such that in particular the electrical terminals of two capacitors according to the invention are arranged offset relative to one another in the circumferential direction when the second outer sides of the housing of the two capacitors contact each another, congruently.

It is furthermore provided in accordance with an embodiment of the capacitor according to the invention that the capacitor is an electrolytic capacitor. In accordance with further embodiments, the capacitor is a tantalum electrolytic capacitor or an aluminium electrolytic capacitor.

In accordance with a further aspect of the invention a capacitor assembly is disclosed, having a plurality of capacitors, wherein each capacitor is formed by a capacitor according to the invention. The capacitors are stacked one on top of the other, such that each capacitor contacts with its first or with its second outer side the first or the second outer side of an adjacent capacitor of the capacitor assembly.

In accordance with an embodiment of the capacitor assembly according to the invention it is provided that the capacitor assembly comprises three capacitors according to the invention, more specifically a first outer capacitor, a second middle capacitor, and a third outer capacitor. The second capacitor is arranged between the two outer capacitors, and the second capacitor contacts with its second side the second side of the third capacitor. The second capacitor contacts with its first side a second side of the first capacitor.

It is furthermore provided in accordance with an embodiment of the capacitor assembly according to the invention that the electrical terminal of the third capacitor is arranged offset relative to the electrical terminals of the first and of the second capacitor of the capacitor assembly.

A further aspect of the present invention relates to an implantable medical device having a device housing which surrounds an interior. The interior has an arcuate inner side, and at least one capacitor according to the invention is arranged in the interior. The second portion of the lateral outer side of the housing of the at least one capacitor extends along the inner side of the device housing (following the arcuate course of the inner side) and in particular faces same.

Lastly, a further aspect of the present invention relates to an implantable medical device, comprising a device housing which surrounds an interior. The device housing has an arcuate inner side, which is formed by an arcuate lateral wall of the device housing. A capacitor assembly according to the invention is arranged in the interior, and the second portion of the lateral outer side of the housing of the capacitor in question extends along the inner side of the device housing and in particular faces same.

Other features which are considered as characteristic for the invention are set forth in the appended claims.

Although the invention is illustrated and described herein as embodied in a stackable capacitor for an implantable medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 is a perspective view of an embodiment of an implantable medical device according to the invention;

FIG. 5 is a perspective view of the capacitor assembly according to FIG. 1, wherein FIG. 5 illustrates a position of the capacitor assembly in the device housing shown in FIG. 4.

DETAILED DESCRIPTION OF THE INVENTION

Figure 1:
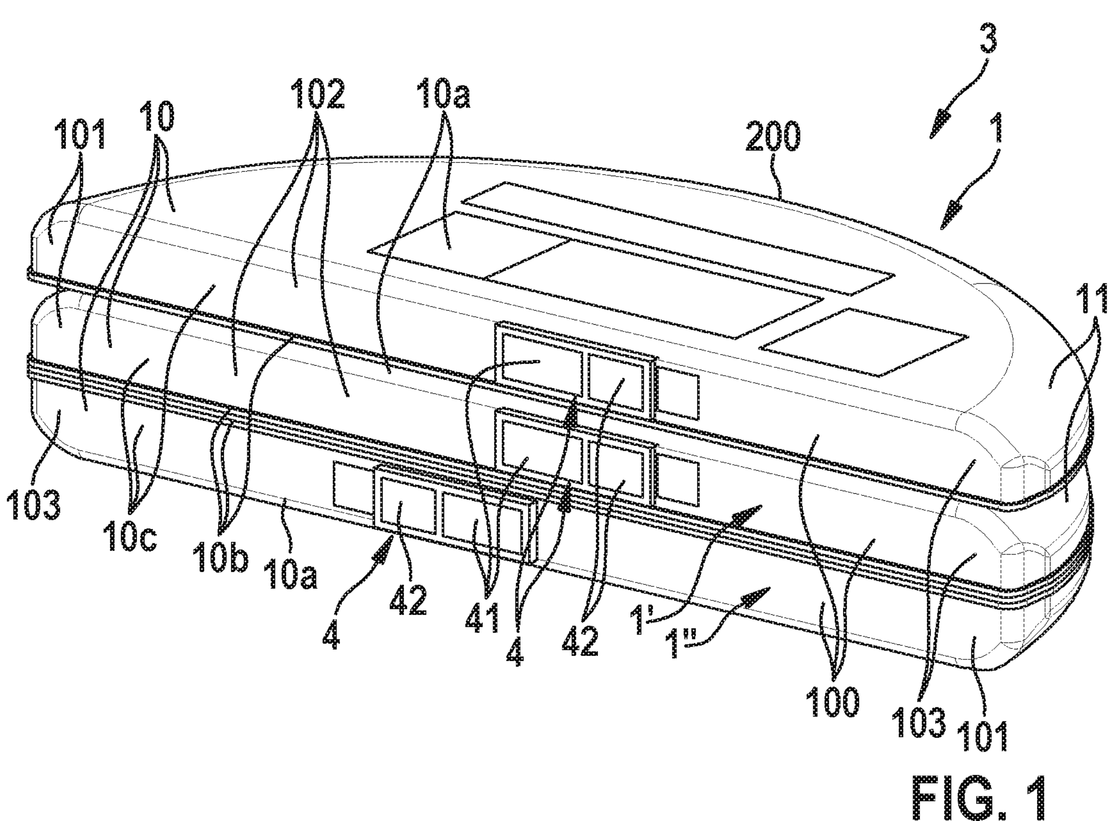
FIG. 1 is a diagrammatic, perspective view of an embodiment of a capacitor assembly according to the invention in a form of a stack of three capacitors according to the invention.
Figure 2:
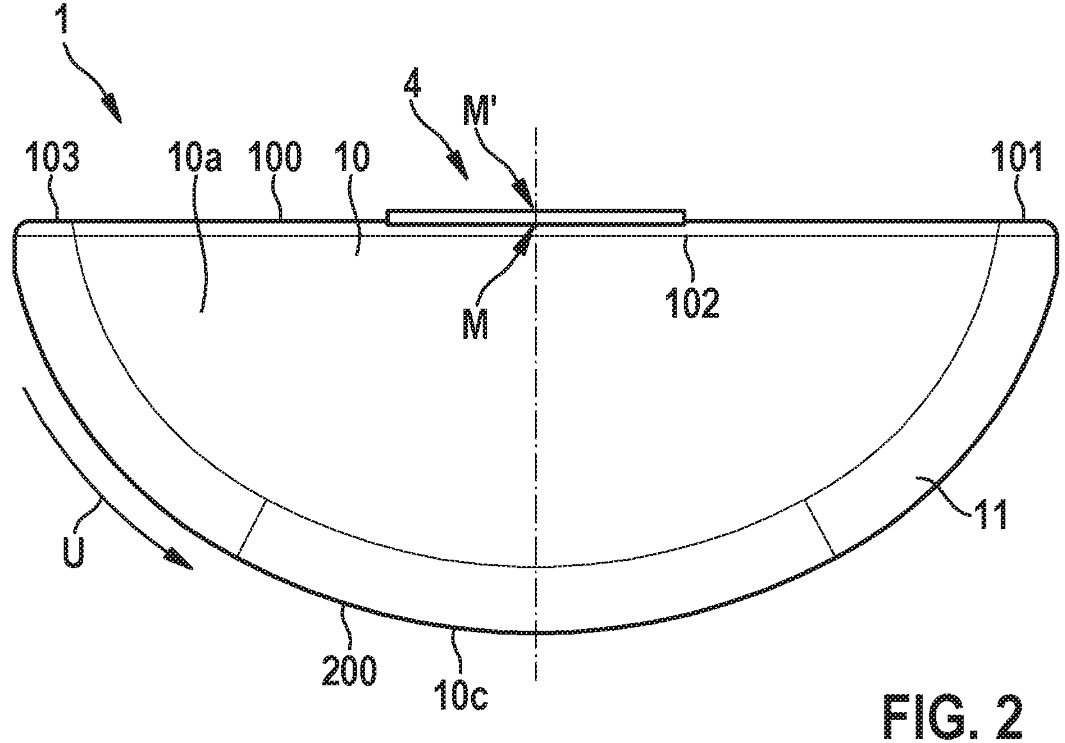
FIG. 2 is a plan view of an embodiment of the capacitor according to the invention.

Referring now to the figures of the drawings in detail and first, particularly to FIGS. 1 and 2 thereof, there is shown an embodiment of a capacitor 1 which can be used for an implantable medical device 2, for example in the form of an implantable cardioverter defibrillator (ICD).

It is provided that the capacitor 1 has a housing 10, wherein the housing 10 has a first outer side 10*a* and a second outer side 10*b* facing away from the first outer side 10*a*. The two outer sides 10*a*, 10*b* are connected to one another via a lateral outer side 10*c* of the housing 10 running in a circumferential direction U of the housing 10, and the lateral outer side 10*c* has a straight first portion 100 and arcuate second portion 200. The first portion 100 has two end regions 101, 103, which are connected to one another via a middle region 102 of the first portion 100, wherein the end regions 101, 103 are each connected to the second portion 200. The capacitor 1 has an electrical terminal 4 arranged on the middle region 102 of the first portion 100 of the lateral outer side 10*c*, which electrical terminal has two contact surfaces 41, 42 for electrically contacting the capacitor 1.

The housing 10 of the capacitor 1 is preferably symmetrically identical with respect to a plane of symmetry E, which in accordance with FIG. 2 runs perpendicularly to the first portion 100 of the lateral outer side 10*c* and perpendicularly to the first and the second outer side 10*a*, 10*b*. It is preferably provided that the two outer sides 10*a*, 10*b* are semi-circular. It is furthermore preferably provided, as can be seen in particular with reference to FIG. 1, that the arcuate second portion 200 of the lateral outer side 10*c* forms, with the first outer side 10*a*, an arcuate rounded housing edge 11 of the housing 10 of the capacitor 1.

By rotating the capacitor 1 through 180° it can be used both as the upper and lower capacitor 1, 1" in the stack. This is made possible due to the symmetrical design of the capacitor outer contour, so that, after having been rotated, it is congruent with the non-rotated capacitors.

Due to the arrangement of the electrical terminal 4 of the capacitor 1, the terminals 4 in the stack come to lie closely relative to one another, so that the through-wiring can be provided in a compact way. If the terminal 4 were arranged for example in an end region 101, 103 of the first portion 100 of the lateral outer side 10*c*, the terminal 4, after a 180° rotation of the capacitor 1, would be located at the opposite end of the capacitor stack.

Due to a slightly eccentric positioning of the terminals 4, it is furthermore achieved that the terminals 4 are positioned closely enough together in the stack to achieve very short conductor track paths (low-loss connection due to low electrical resistance), yet a mix-up-free arrangement still can be provided. A mix-up-free connection to the wiring strip is necessary so that the correct electrical polarisation can be observed. The eccentric arrangement of the terminal 4 is provided in accordance with FIG. 1 by arranging the center point M' of the electrical terminal 4 of each capacitor slightly offset in the circumferential direction U relative to the center point M of the first portion 100.

Figure 3A:
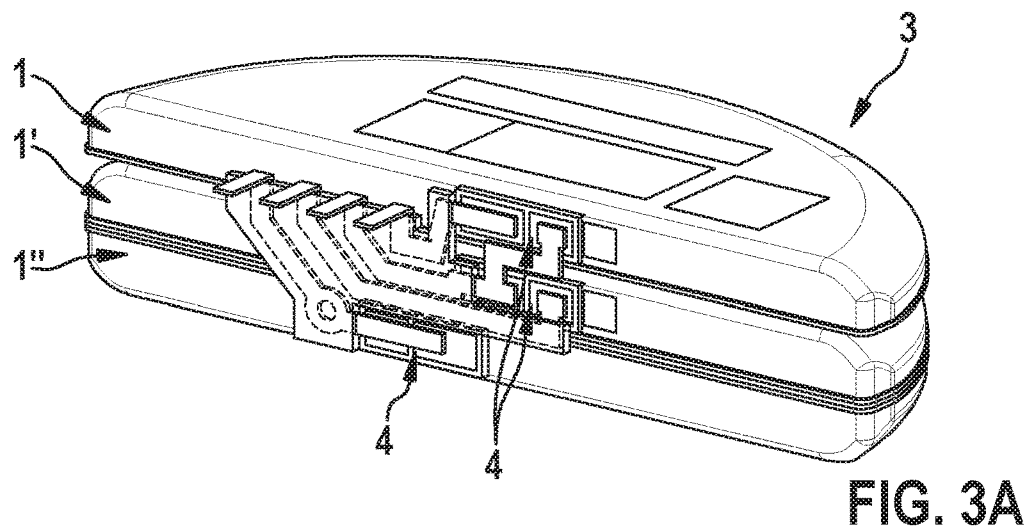
FIGS. 3A-3C are perspective views showing a view of three stacks of three capacitors as per FIG. 2, wherein electrical terminals of the capacitors are arranged such that a mix-up-free assembly of the capacitors is supported.
Figure 3B:
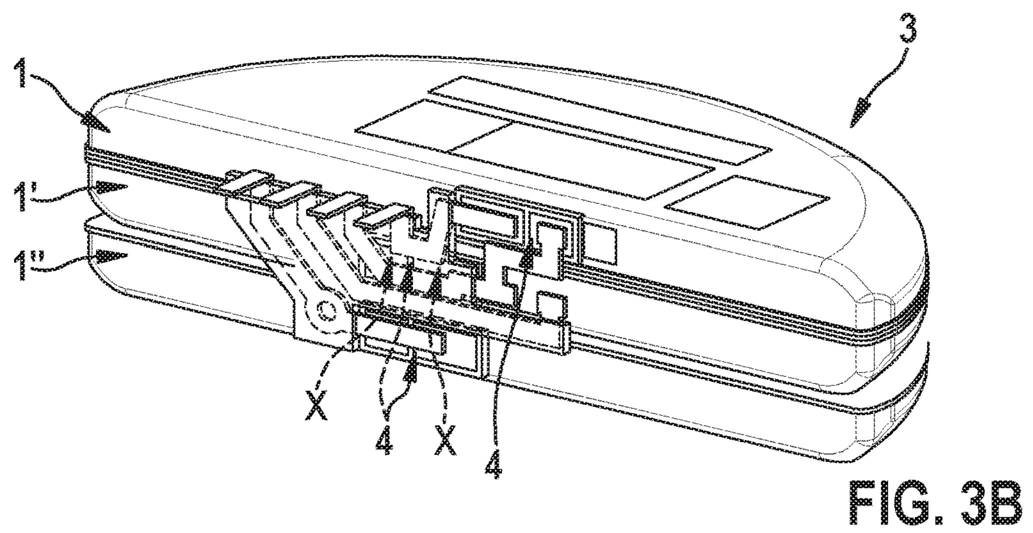
Figure 3C:
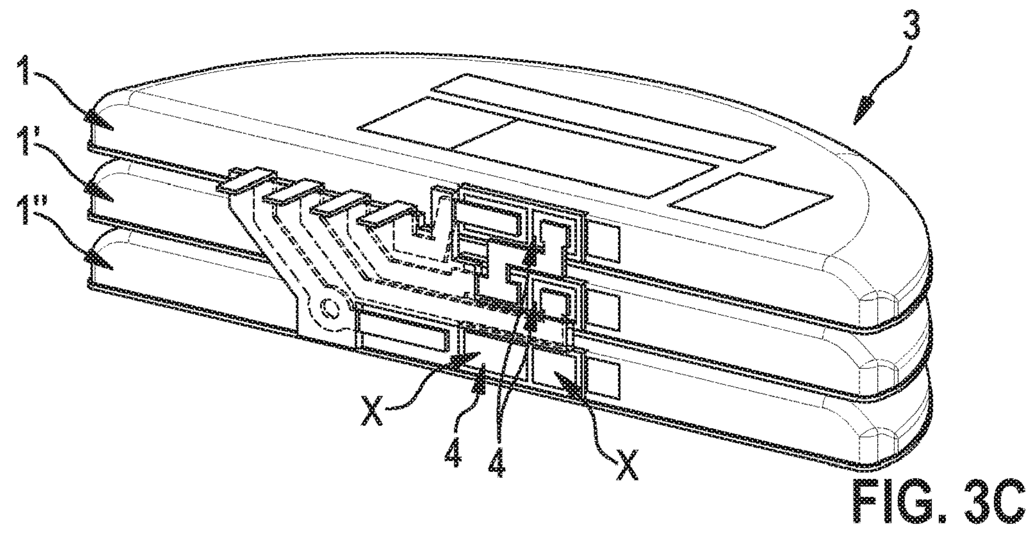

The desired normal state, i.e. a correctly wired capacitor assembly in the form of a capacitor stack, is shown in FIG. 3A. FIG. 3B by contrast shows a situation in which the middle capacitor 1' is arranged rotated or the entire stack is rotated through 180°. Here, on account of the particular positioning of the terminals 4, no welding of the terminals 4, X is possible. Lastly, FIG. 3C shows a situation in which none of the capacitors 1, 1', 1" is arranged rotated. Here as well, wiring is not possible. Furthermore, the defective arrangement according to FIG. 3C also does not allow assembly of the stack 3 in the device housing 20 of the implant 2, since the sharp-edged stack lower side 10*b* does not fit into the rounded device housing 20.

Figure 6A:
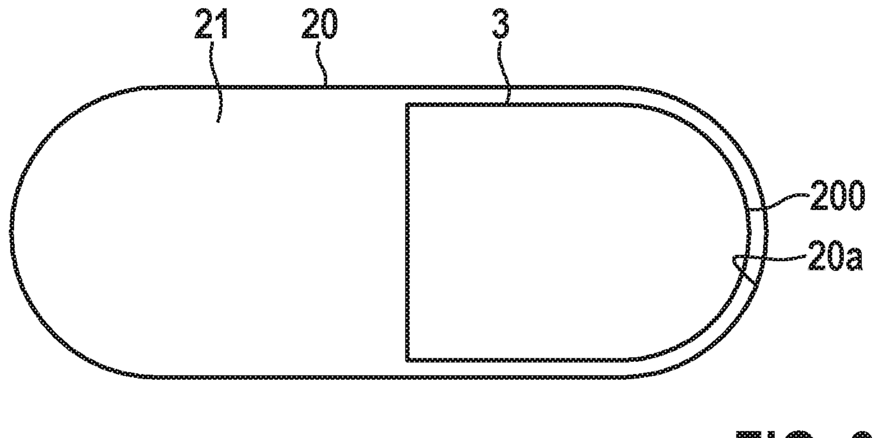
FIGS. 6A-6B show a schematic depiction of an arrangement of a capacitor stack with an arcuate outer side (FIG. 6A) and of a cuboid capacitor stack (FIG. 6B) in a device housing with arcuate side wall.

FIGS. 4 to 6 lastly illustrate the arrangement of the capacitors 1, 1', 1" or the capacitor assembly in the interior 21 of the device housing 20 of the implantable medical device 2 shown in FIG. 4, which in this case is an ICD 2, which also has a header 22, via which electrodes (not shown) of the device 2 can be electrically conductively connected to components of the device 2 arranged in the interior 21 of the device housing 20.

Figure 6B:
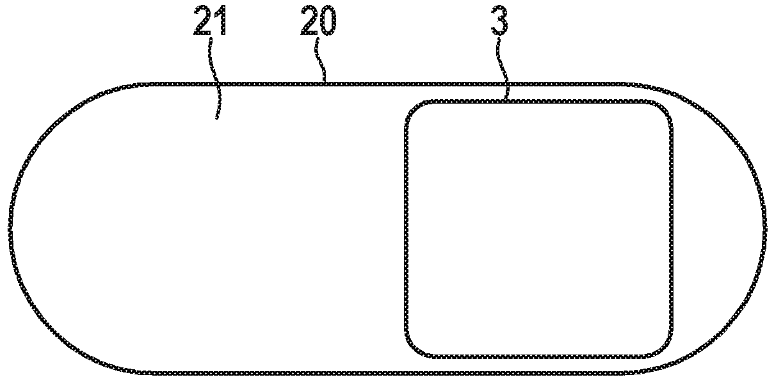

FIG. 5 shows the capacitor stack 3 without the device housing 20, wherein it can be seen that the arcuately extended second portion 200 of the lateral side 10*c* of each capacitor follows an arcuate inner side 20*a* of the device housing, such that a space-saving arrangement of the capacitor assembly in the interior 21 of the device housing 20 is attained. This arrangement is shown schematically also in FIG. 6A. FIG. 6B by contrast shows the less advantageous arrangement of a cuboid capacitor stack 3' in a device housing 21 with arcuate inner side or side wall 20*a*.

The solution according to the invention advantageously allows a volume-efficient arrangement of the capacitors 1, 1', 1" in the device housing 20 of the implant 2. The radius of the rounding of the edge 11 preferably lies above 2 mm. As a result of the invention, a reduction of the component diversity and of the development costs is furthermore achieved, since only one capacitor variant is used in the stack 3. A mix-up-free assembly is possible due to the design of the terminals 4.

The invention claimed is:

1. A capacitor assembly, comprising:

three structurally identical capacitors, each of said structurally identical capacitors containing:

a housing having a first outer side, a second outer side facing away from said first outer side, and a lateral outer side running in a circumferential direction of said housing, said first and second outer sides being connected to one another via said lateral outer side running in the circumferential direction of said housing, said lateral outer side having a straight first portion and an arcuate second portion, said straight first portion having a middle region and two end regions, which are connected to one another via said middle region of said straight first portion, and said end regions are each connected to said arcuate second portion; and an electrical terminal disposed on said middle region of said straight first portion of said lateral outer side, said electrical terminal having two planar contact surfaces for electrically contacting said capacitor;

said arcuate second portion of said lateral outer side forming, with said first outer side, a rounded housing edge of said housing of the capacitor;

a substantially flat wiring strip including a plurality of conductor tracks being connected to the electrical terminals of said three structurally identical capacitors;

said structurally identical capacitors being disposed stacked one above the other so that each of said structurally identical capacitors contacts with said first outer side or via said second outer side said first outer side or said second outer side of an adjacent one of said structurally identical capacitors of the capacitor assembly;

said structurally identical capacitors including a first outer capacitor, a second middle capacitor, and a third outer capacitor, said second middle capacitor being disposed between said first and third outer capacitors, said second middle capacitor contacting with said second outer side of said third outer capacitor, and said second middle capacitor contacts with said first outer side or said second outer side of said first outer capacitor; and said electrical terminal of said third outer capacitor being disposed offset relative to said electrical terminal of said first outer capacitor and said second middle capacitor of the capacitor assembly.

2. The capacitor assembly according to claim 1, wherein said housing is symmetrically identical with respect to a plane of symmetry, which runs perpendicularly to said straight first portion of said lateral outer side and perpendicularly to said first outer side and said second outer side.

3. The capacitor assembly according to claim 1, wherein said first outer side and/or said second outer side is semi-circular.

4. The capacitor assembly according to claim 1, wherein the capacitors are electrolytic capacitors.

5. The capacitor assembly according to claim 1, wherein the first portion of the lateral outer side has a center point in the circumferential direction, and in that the electrical terminal has a center point in the circumferential direction, and the center point of the electrical terminal in the circumferential direction is disposed offset relative to the center point of the first portion.

6. An implantable medical device, comprising:

a device housing surrounding an interior, wherein said device housing having an arcuate inner side;

a capacitor assembly according to claim 1 disposed in said interior; and said second portion of said lateral outer side of said housing of each of said capacitors extending along said arcuate inner side of said device housing.

* * * * *